(12) United States Patent
Graf et al.

(10) Patent No.: US 9,314,236 B2
(45) Date of Patent: Apr. 19, 2016

(54) TISSUE GRAFT FIXATION

(75) Inventors: Ben Graf, Madison, WI (US); Jason LeBeau, Fall River, MA (US)

(73) Assignee: Smith & Nephew, Inc., Memphis, TN (US)

( * ) Notice: Subject to any disclaimer, the term of this patent is extended or adjusted under 35 U.S.C. 154(b) by 1463 days.

(21) Appl. No.: 11/688,447

(22) Filed: Mar. 20, 2007

(65) Prior Publication Data
US 2007/0233241 A1  Oct. 4, 2007

Related U.S. Application Data

(60) Provisional application No. 60/783,403, filed on Mar. 20, 2006.

(51) Int. Cl.
*A61F 2/08* (2006.01)
*A61B 17/04* (2006.01)

(52) U.S. Cl.
CPC ..... *A61B 17/0401* (2013.01); *A61B 2017/0404* (2013.01); *A61F 2002/0852* (2013.01); *A61F 2002/0882* (2013.01)

(58) Field of Classification Search
CPC .............. A61B 17/0401; A61F 2/0811; A61F 2002/0882
USPC ................ 606/300–321, 232; 623/13.11–13.2
See application file for complete search history.

(56) References Cited

U.S. PATENT DOCUMENTS

| 5,306,301 | A |   | 4/1994 | Graf et al. |  |
|---|---|---|---|---|---|
| 5,733,307 | A | * | 3/1998 | Dinsdale | 606/232 |
| 5,769,894 | A | * | 6/1998 | Ferragamo | 606/148 |
| 6,086,591 | A | * | 7/2000 | Bojarski | 606/64 |
| 6,440,134 | B1 | * | 8/2002 | Zaccherotti et al. | 606/232 |
| 6,533,802 | B2 | * | 3/2003 | Bojarski et al. | 606/232 |
| 6,902,573 | B2 | * | 6/2005 | Strobel et al. | 606/232 |
| 7,097,654 | B1 | * | 8/2006 | Freedland | 606/232 |
| 2003/0130694 | A1 | * | 7/2003 | Bojarski et al. | 606/228 |

(Continued)

FOREIGN PATENT DOCUMENTS

| JP | 06114081 | 4/1994 |
|---|---|---|
| JP | 08507462 | 8/1996 |

(Continued)

OTHER PUBLICATIONS

International Search Report and Written Opinion for PCT/US2007/064397 Dated Aug. 10, 2007.
Notice of Reasons for Rejection for Japanese Application No. 2009-501697, mailed Feb. 21, 2012.

*Primary Examiner* — Matthew Lawson
(74) *Attorney, Agent, or Firm* — Burns & Levinson LLP; Joseph M. Maraia

(57) ABSTRACT

The present disclosure relates to a graft fixation device including a body configured and arranged for passage through a bone tunnel when oriented generally longitudinally with respect to the bone tunnel, and for residing against bone defining an opening to the bone tunnel when oriented generally transversely with respect to the bone tunnel. The body defines an enclosed channel for receiving a member such that the member is substantially evenly distributed about a longitudinal extent of the body so that the body maintains a generally longitudinal orientation during passage through the tunnel, and includes a cross bar about which the member is looped when the body resides against the bone defining the opening to the bone tunnel.

3 Claims, 7 Drawing Sheets

(56) References Cited

U.S. PATENT DOCUMENTS

2004/0015171 A1* 1/2004 Bojarski et al. ............... 606/72
2004/0153153 A1* 8/2004 Elson et al. ................ 623/13.14
2005/0065533 A1* 3/2005 Magen et al. ................ 606/102
2006/0190041 A1* 8/2006 Fallin et al. .................. 606/232
2006/0229722 A1* 10/2006 Bianchi et al. ............ 623/13.14

FOREIGN PATENT DOCUMENTS

| WO | WO9518571 A1 | 7/1995 |
| WO | WO0044310 A1 | 8/2000 |
| WO | WO0149190 A | 7/2001 |
| WO | WO02091959 A | 11/2002 |

* cited by examiner

TISSUE GRAFT FIXATION

CROSS REFERENCE TO RELATED APPLICATIONS

This application claims the benefit of U.S. Provisional Application No. 60/783,403, filed Mar. 20, 2006, the disclosure of which is incorporated herein by reference in its entirety.

TECHNICAL FIELD

This present disclosure relates to tissue graft fixation.

BACKGROUND

A ligament, such as an anterior cruciate ligament (ACL), that has ruptured and is non-repairable, is generally replaced arthroscopically by a tissue graft. The tissue graft can be harvested from a portion of a patellar tendon having so called "bone blocks" at each end, and from the semitendonosis and gracilis. Alternatively, the tissue graft can be formed from synthetic materials or from a combination of synthetic and natural materials.

The replacement tissue graft is implanted by securing one end of the tissue graft in a socket formed in a passage within the femur, and passing the other end of the graft through a passage formed in the tibia. Generally, sutures are used to affix each end of the tissue graft to a fastener (e.g., an interference screw or a post), which is then secured to the bone.

It is also known to use a graft fixation member, e.g., a fixation button, to secure the tissue graft at the femoral cortex, as described in U.S. Pat. No. 5,306,301 ("the '301 patent") hereby incorporated by reference in its entirety. The graft fixation member is coupled to the tissue graft and a suture, or other pulling means, is used to pull the fixation member/tissue graft combination through the bone tunnel. However, these fixation members can be cumbersome to use, due to the hole and suture loop placements on the member making it difficult to pass the graft through the tunnel. In addition, the member comes in various sizes, which makes it difficult to center the member on the top opening of the femoral tunnel. Furthermore, as the member is being drawn through the bone tunnel, the member frequently rotates off-axis, rather than maintaining a generally longitudinal orientation.

SUMMARY

According to one aspect, a graft fixation device includes a body configured and arranged for passage through a bone tunnel when oriented generally longitudinally with respect to the bone tunnel, and for residing against bone defining an opening to the bone tunnel when oriented generally transversely with respect to the bone tunnel. The body defines an enclosed channel configured for receiving a tissue graft such that the tissue graft is substantially evenly distributed about a longitudinal extent of the body so that the body maintains a generally longitudinal orientation during passage through the tunnel, and includes a cross bar about which the tissue graft is looped when the body resides against the bone defining the opening to the bone tunnel.

In an embodiment, the body includes a leading end portion defining a hole, and a trailing end portion defining a hole. In another embodiment, the trailing end portion has an open end or a closed end. In a further embodiment, the trailing end portion has a closed end wherein the closed end is angled relative to the body at an angle α, which is about 45 degrees. In yet a further embodiment, the body includes a trailing end portion having an open end and a leading end portion having an open end.

In another aspect, a graft fixation device includes an intermediate portion having at least two tabs, the tabs extending transverse to the intermediate portion, the intermediate portion including at least one hole, the hole being located between the tabs.

In an embodiment, the device further includes a first end portion including at least one hole and a second end portion including at least one hole. In another embodiment, intermediate portion includes at least two holes. In yet another embodiment, the graft fixation device further includes a continuous loop of material passing through the hole of the intermediate portion. The material may include a suture.

In yet another aspect, a graft fixation device includes an intermediate portion including a hinge coupled to the intermediate portion, the hinge and the intermediate portion defining a channel configured for receiving a tissue graft.

In an embodiment, the device further includes a first end portion having at least one hole and a second end portion having at least one hole. In another embodiment, the hinge is U-shaped. In yet another embodiment, the hinge is rotatable relative to the fixation device.

In another general aspect, a method includes looping a graft through an opening in a graft fixation device, and pulling the graft fixation device and looped graft through a bone tunnel. The graft fixation device is maintained substantially longitudinally oriented relative to the tunnel while being pulled through the bone tunnel.

Embodiments of this aspect may include drilling at least one bone tunnel extending in a generally lateral direction through a knee joint. In yet another embodiment, the method further includes looping grafts through openings in multiple graft fixation devices, drilling multiple bone tunnels extending in a generally lateral direction through a knee joint, and pulling each of the graft fixation devices and looped grafts through the bone tunnels. The graft fixation devices are each configured such that the graft fixation devices are maintained substantially longitudinally oriented relative to the tunnels while being pulled through the tunnels.

In a further aspect, a method includes providing a graft fixation device having an intermediate portion including at least two tabs, the tabs extending transverse to the intermediate portion, the intermediate portion including at least one hole, the hole being located between the tabs and including a continuous loop of material, drilling a bone tunnel extending in a generally lateral direction through a knee joint, looping a tissue graft through the continuous loop of material such that the tissue graft is situated between the tabs, and pulling the graft fixation device and looped graft through the bone tunnel, the graft fixation device being configured such that the graft fixation device is maintained substantially longitudinally oriented relative to the tunnel while being pulled through the bone tunnel. The material may include a suture.

In an embodiment, the method further includes placing the fixation member over an opening to the bone tunnel such that the tabs extend into the bone tunnel. In another embodiment, the graft fixation device further includes a first end portion including at least one hole and a second end portion including at least one hole.

In yet another embodiment, method further includes providing multiple graft fixation devices, each graft fixation device having an intermediate portion including at least two tabs, the tabs extending transverse to the intermediate portion, the intermediate portion including at least one hole, the hole being located between the tabs and including a continuous loop of material, drilling multiple bone tunnels extending in a generally lateral direction through a knee joint, looping a tissue graft through each of the continuous loop of material such that the tissue graft is situated between the tabs of each of the graft fixation devices, and pulling the graft fixation devices and looped grafts through the bone tunnels, the graft fixation devices being configured such that the graft fixation devices are maintained substantially longitudinally oriented relative to the tunnels while being pulled through the tunnels. Each of the graft fixation devices may further include a first end portion having at least one hole and a second end portion having at least one hole.

In yet a further aspect, a method includes providing a graft fixation device having an intermediate portion having a rotatable hinge coupled to the intermediate portion, the hinge and the intermediate portion defining a channel configured for receiving a tissue graft; drilling a bone tunnel extending in a generally lateral direction through a knee joint; looping a tissue graft through the channel; and pulling the graft fixation device and looped graft through the bone tunnel, the graft fixation device being configured such that the graft fixation device is maintained substantially longitudinally oriented relative to the tunnel while being pulled through the bone tunnel.

In an embodiment, the method further includes rotating the hinge relative to the fixation member and placing the fixation member over an opening to the bone tunnel such that the hinge extends into the bone tunnel. In another embodiment, the graft fixation device further includes a first end portion including at least one hole and a second end portion including at least one hole.

In yet another embodiment, the method further includes providing multiple graft fixation devices, each graft fixation device including an intermediate portion having a rotatable hinge coupled to the intermediate portion, the hinge and the intermediate portion defining a channel for receiving a tissue graft; drilling multiple bone tunnels extending in a generally lateral direction through a knee joint; looping a tissue graft through each of the channels of the multiple graft fixation devices; and pulling each of the graft fixation devices and looped grafts through the multiple bone tunnels, the graft fixation devices being configured such that each graft fixation device is maintained substantially longitudinally oriented relative to the tunnels while being pulled through the tunnels. Each of the graft fixation devices may further include a first end portion including at least one hole and a second portion including at least one hole.

In another aspect, a graft fixation device includes an intermediate portion having a prominence on a surface of the intermediate portion. The prominence facilitates alignment of a tissue graft with the device as the device is being pulled through a bone tunnel.

Advantages may include one or more of the following features. Because the tissue graft or suture attached to the fixation member is preferably evenly distributed about the longitudinal extent of the fixation member, the fixation member is advantageously centered within the bone tunnel during passage through the bone tunnel, thus limiting any tendency of the fixation member to snag on the bone tunnel wall. The cross-bar, tabs, and hinge all facilitate centering of the graft or suture relative to the opening to the bone tunnel, thus limiting any tendency of the tissue graft or suture to kink against the bone cortex.

The details of one or more embodiments of the present disclosure are set forth in the accompanying drawings and the description below. Other features, objects, and advantages of the present disclosure will be apparent from the description and drawings, and from the claims.

DETAILED DESCRIPTION

Figure 1:
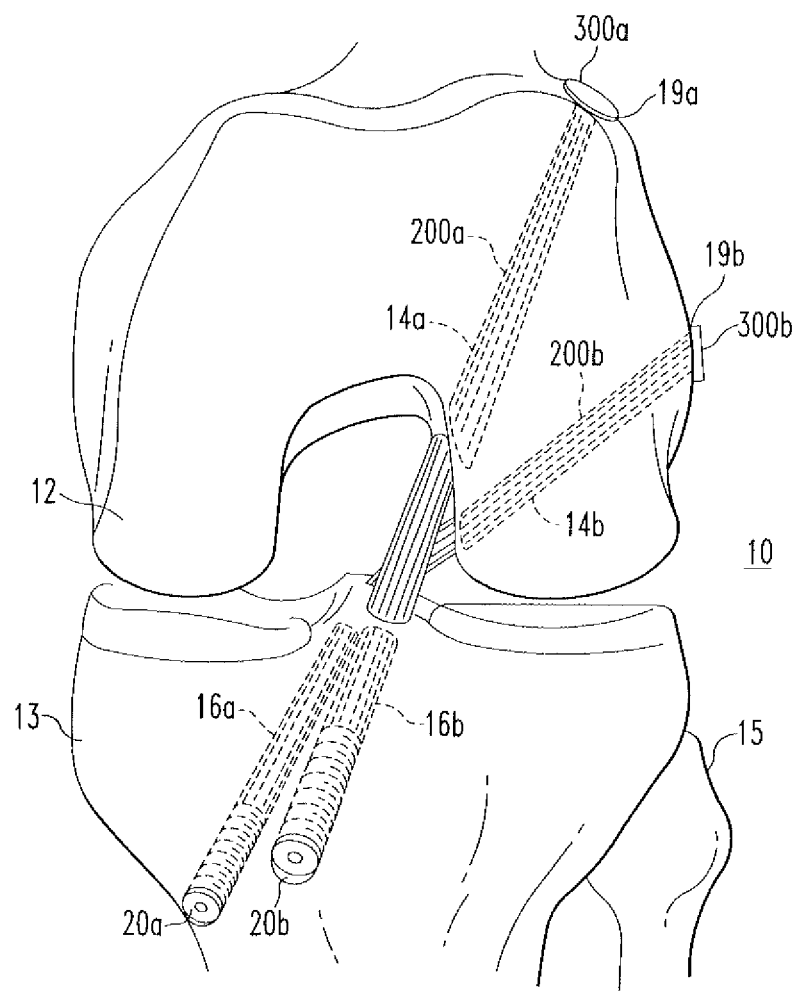
FIG. 1 shows a tissue graft secured within tibia and femoral bone tunnels during an ACL reconstruction procedure.

Referring to FIG. 1, during a multiple-bundle, ligament repair and reconstruction procedure, tissue grafts 200a, 200b are secured at openings 19a, 19b to femoral channels 14a, 14b within a knee 100 using graft fixation members 300a, 300b, respectively. The tissue grafts 200a, 200b are tensioned at opposing ends of the channels 14a, 14b from the fixation member 300a, 300b by a surgeon and secured in place with bone anchors 20a, 20b within tibial channels 16a, 16b.

The use of a multiple-bundle technique, e.g., more than one femoral channel 14, tibial channel 16, tissue graft 200 and fixation member 300, results in a repaired joint that is more anatomically correct than a single bundle technique, e.g., a single femoral channel 14, tissue graft 200 and fixation member 300. The multiple-bundle technique results in multiple anchor points to transfer stresses evenly across the knee joint and/or permits a surgeon to drill femoral and tibial channels that are more laterally oriented, closer to the joint between the tibia 13 and fibia 15, and shallower than bone channels that are typically drilled farther away from the knee joint, and thus deeper. Further, securing the tissue grafts 200a, 200b directly to the fixation members 300a, 300b permits the surgeon to drill shallower bone channels than what may be possible when intermediate suture is used to connect a tissue graft to a fixation member, and due to the larger size of the fixation member as compared to conventional fixation members, such as the Endobutton CL, product no. 7209352, available from Smith & Nephew, Inc., permits the bone tunnels to have a uniform cross-section that receives both the tissue graft and the fixation member to lie over the larger sized bone tunnel when the fixation member is positioned against the cortex at the opening to the femoral tunnel.

Figure 2A:
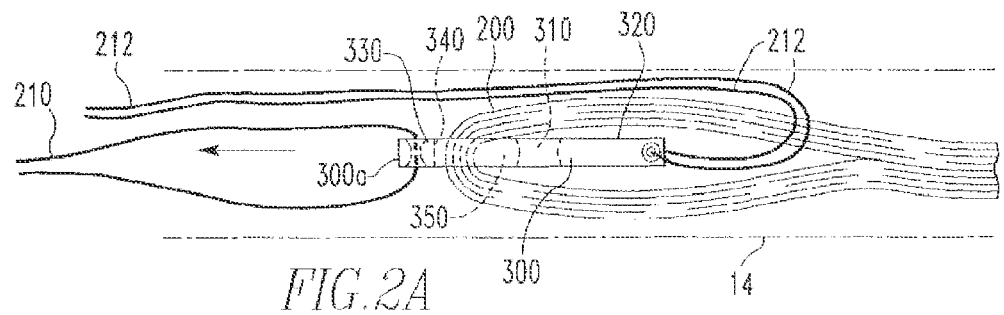
FIG. 2A is a side view of a fixation member shown drawing the tissue graft through the femoral bone tunnel.

As shown in FIG. 2A, the tissue graft 200 is looped through an opening 350 in the fixation member 300 and is pulled through a tibia channel 16 and the femoral channel 14 using a suture 210 passed through a hole 340 defined in a leading end 300a of the graft fixation member 300.

During passage through the channels 14 and 16, the fixation member 300 is oriented longitudinally within the channels. To limit any tendency of the fixation member 300 to become oriented off-axis of the channels 14, 16, the tissue graft 200 is looped through the fixation member such that the tissue graft 200 is evenly distributed on either side of the fixation member 300 as the fixation member is pulled through the channels.

Figure 2B:
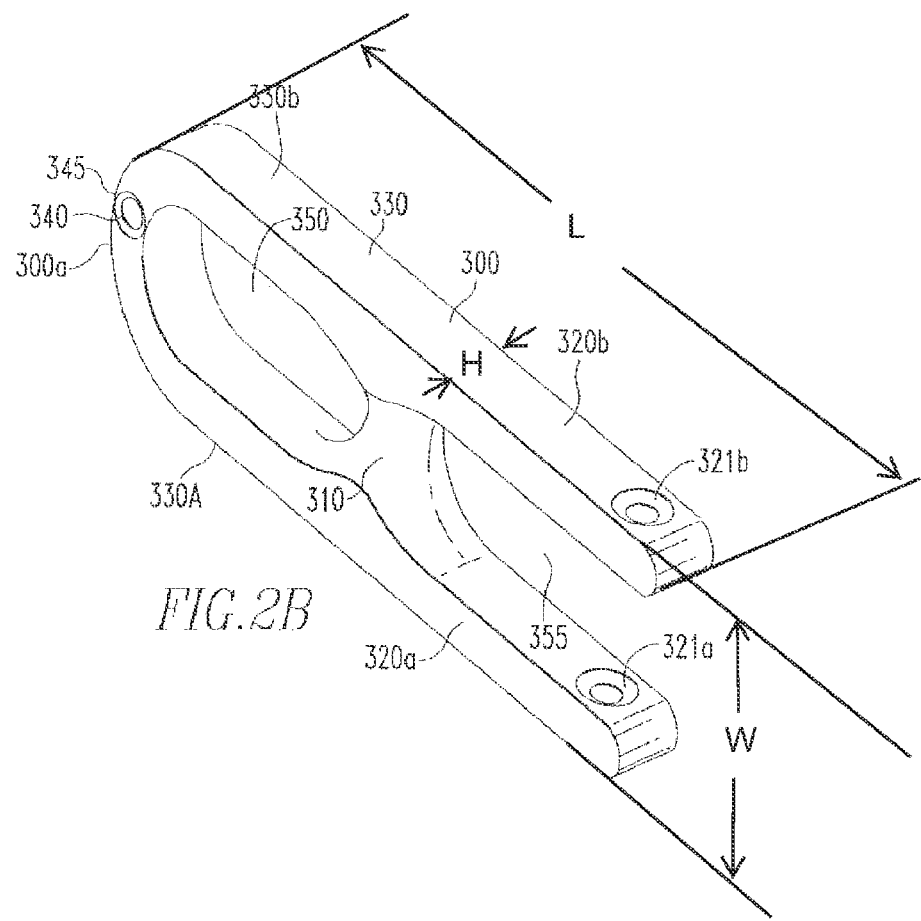
FIG. 2B is a perspective view of the fixation member of FIG. 2A.

Referring to FIG. 2B, the fixation member 300 is an elongated member having a transversely extending cross bar 310, a longitudinally extending trailing end portion 320, and a longitudinally extending leading end portion 330. The trailing end portion 320 includes a pair of rectangular arms 320a, 320b extending from the cross bar 310 and defining an open-ended, tissue graft channel 355 therebetween. The arms 320a, 320b each define one of opposing holes 321a, 321b for receiving one or more strands of suture 212, which is used to flip the fixation member 300 after passage through the femoral tunnel 14 such that the fixation member 300 is positioned against the femur and centered about the femoral opening, as described further below.

The leading end portion 330 includes a pair of rectangular arms 330a, 330b joined by a curved portion 345 which collectively define an oval-shaped, closed-end, tissue graft opening 350. The tissue graft 200 is looped through graft opening 350 with the closed-end of the leading end portion ensuring that the graft 200 remains connected to the fixation member 300. The curved portion 345 defines the suture hole 340. Rather than having a closed end the leading end portion 330 may also be open, similar to the trailing end portion 320. In this embodiment, the fixation member would be in the shape of an "H" and each end would include a pair of rectangular arms having opposing holes for receiving one or more strands of suture.

The cross bar 310 acts as a fulcrum for the tissue graft 200 within the bone channels after passage of the fixation member through the channels and positioning of the fixation member against the femoral cortex, as well as allowing tension to be placed on the tissue graft 200 during subsequent fixation of the tissue graft to the surface of the tibia.

One or more of the cross bar 310, arms 320a, 320b, 330a, 330b and suture openings 321a, 321b, 340 are provided with rounded or chamfered edges to provide a smooth surface for engaging with the tissue graft and/or suture, and thus limiting damage to the tissue graft or suture. By reducing the thickness of the cross bar 310 relative to the remainder of the fixation member, the graft 200 that is wrapped around the cross bar 310 can lie relatively flat as the trailing end of the graft 200 leads away from the fixation member, e.g., thereby ensuring a relatively smooth profile of the combined graft 200 and fixation member 300 within the bone channel 14.

An exemplary fixation member 300 has an overall length (L) of between about 15 mm to about 25 mm, a width (W) of between about 4 mm to about 9 mm, a height (H) of between about 1 mm to about 3 mm, a width or the central bar 310 of between about 1 mm to about 2.5 mm, a length of the leading end channel 350 of between about 5 mm to about 12 mm, a width of the leading end channel 350 of between about 3 mm to about 6 mm, and a thickness of the rectangular end portions 330b of between about 1 mm to about 2 mm.

Other embodiments are within the scope of the following claims.

Figure 3A:
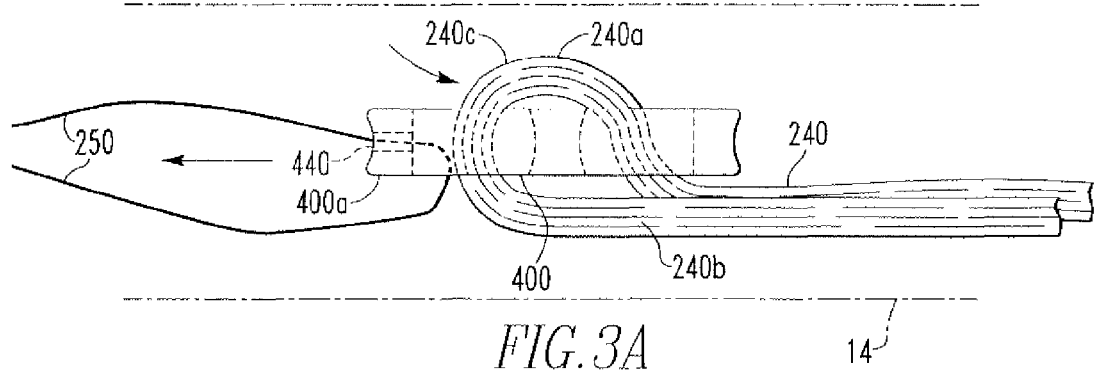
FIG. 3A is a side view of an alternative embodiment of a fixation member shown drawing the tissue graft through the femoral bone tunnel.
Figure 3B:
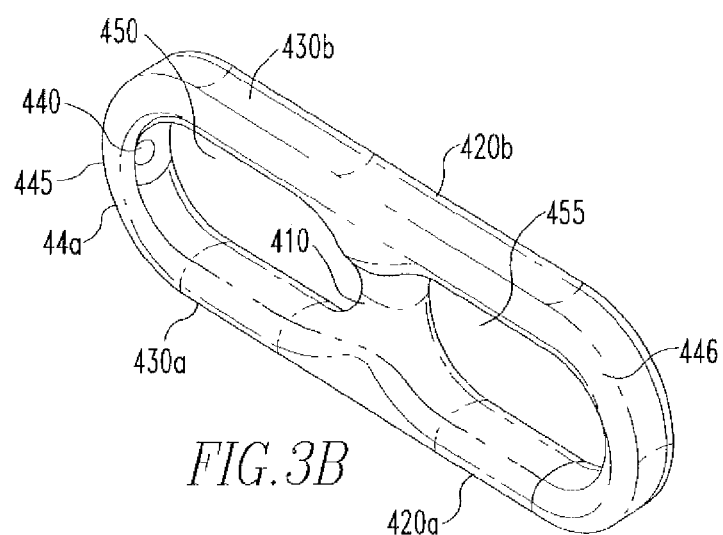
FIG. 3B is a perspective view of the fixation member of FIG. 3A.

For example, referring to FIGS. 3A and 3B, an alternative fixation member 400 includes a cross bar 410 and a leading end 400a defining an opening 440 for passage of a lead suture 250. Rather than including a closed-end channel and an open-ended, tissue graft channel, fixation member 400 includes a pair of closed-end channels 450, 455. The tissue graft 240 is coupled to the fixation member 400 by passing a first section 240a of the tissue graft 240 through the first closed-end channel 450 of the fixation member 400 to form a graft loop 240c which includes the first tissue graft section 240a and a second tissue graft section 240b. The first section 240a of the tissue graft is then passed around the cross bar 410 and back through the second channel 455. Similarly, the lead suture 250 may be looped through the channel 450, rather than being passed through the opening 440.

The fixation member 400 includes a first pair of opposing trailing arms 420a, 420b and a second pair of opposing leading arms 430a, 430b. The first pair of arms 420a, 420b extend longitudinally from the cross bar 410 and are connected by a curved portion 446. The curved portion 446, cross bar 410 and arms 420a, 420b define the second, closed-end channel 455. The second arms 430a, 430 b extend longitudinally from the cross bar 410 in a direction opposite from the first arms 420a, 420b and are connected by a curved portion 445. The second arms 430a, 430b, the cross bar 410 and the curved portion 445 define the first, closed-end channel 450 at the leading end 400a of the fixation member 400. The closed-end channels 450, 455 are each oval-shaped channels that are sized to accommodate the tissue graft ends 240a, 240b. The suture for flipping the fixation member can be looped through channel 455.

Figure 4A:
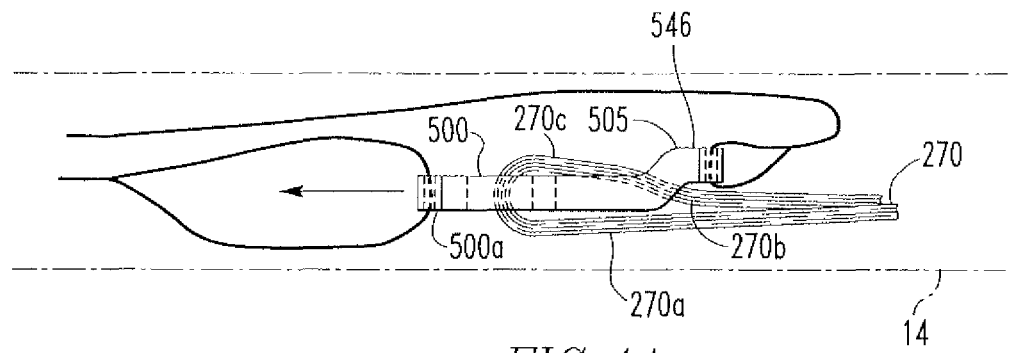
FIG. 4A is a side view of an alternative embodiment of a fixation member shown drawing the tissue graft through the femoral bone tunnel.
Figure 4B:
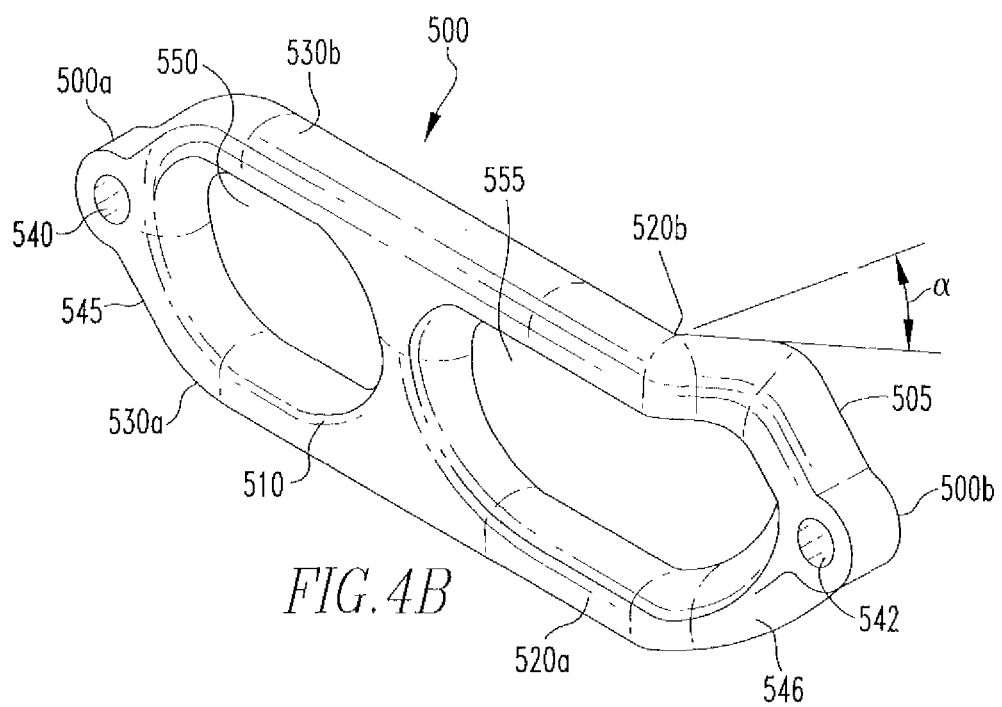
FIG. 4B is a perspective view of the fixation member of FIG. 4A.
Figure 5A:
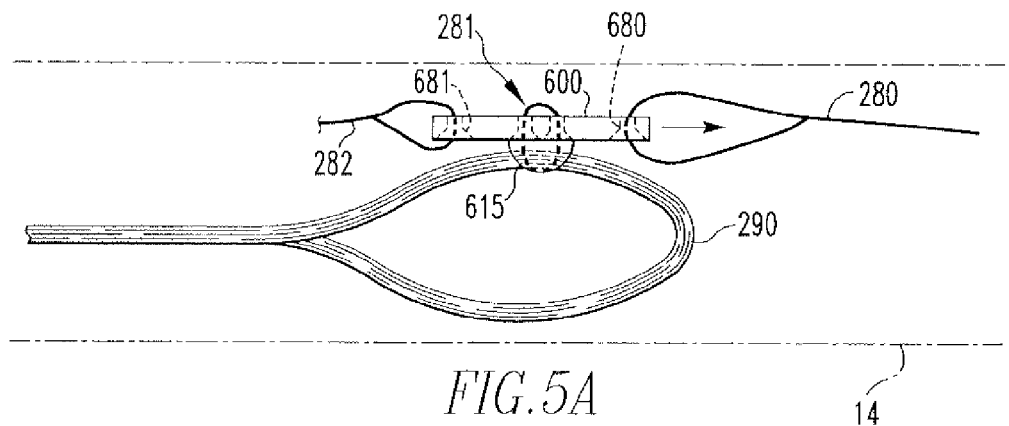
FIG. 5A is a side view of an alternative embodiment of a fixation member shown drawing the tissue graft through the femoral bone tunnel.
Figure 5B:
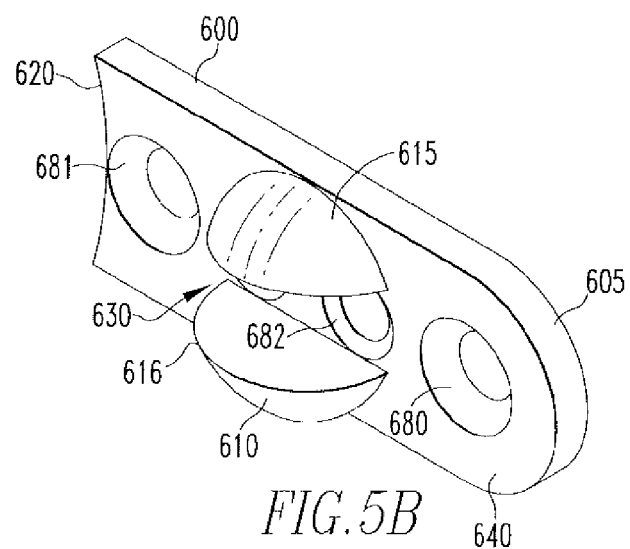
FIG. 5B is a perspective view of the fixation member of FIG. 5A.
Figure 5C:
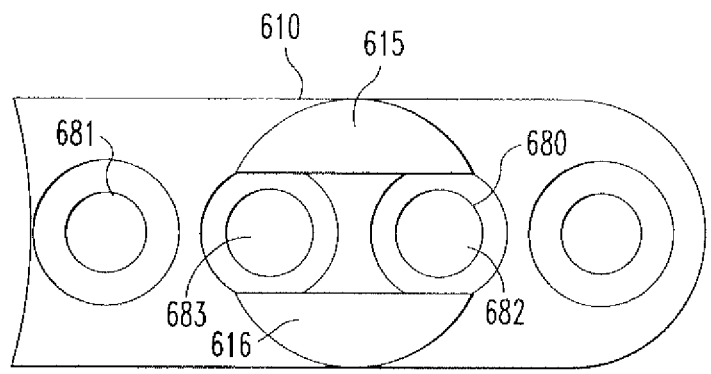
FIG. 5C is a bottom view of the fixation member of FIG. 5A.
Figure 5D:
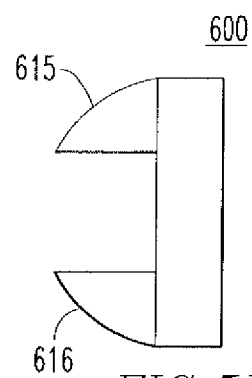
FIG. 5D is an end view of the fixation member of FIG. 5A

Referring to FIGS. 4A and 4B, an alternative fixation member 500 similar to fixation member 400 is coupled with a tissue graft 270 having first and second sections 270a, 270b forming a tissue graft loop 270c. The fixation member 500 includes a leading end portion 500a and a trailing end portion 500b, each defining a respective suture hole 540, 542, with the trailing end portion 500b including an angled portion 505 for accommodating trailing sections of the tissue graft 270. The angled portion 505 facilitates centering of the fixation member 500 within the channels during passage through the channels by allowing the tissue graft to be evenly distributed about the longitudinal axis of the fixation member.

This fixation member 500 defines first and second, generally oval-shaped, closed-end channels 550, 555. The fixation member 500 includes first arms 520a, 520b are connected by a curved portion 545. The first arms are connected by a curved portion 546. The first arms 520a, 520b, cross bar 510, and curved portion 546 define the channel 555. To form angled portion 505, each of the arms 520a, 520b is bent at an angle α, about 45 degrees, relative to the fixation member 500, such that the curved portion 546 extends along a plane parallel to but offset to the remainder of the device. This offset provides space for the graft section 270b as it trails from the fixation member such that the graft is evenly distributed on either side of the fixation member allowing the fixation member to remain centered within the tunnel as it is drawn through the tunnel.

Referring to FIGS. 5A-5D, an alternative fixation member 600 is indirectly coupled to a tissue graft loop 290 by a continuous loop 281 of material passed through central suture holes 682, 683 within an intermediate portion 610 of the fixation member 600. A lead suture 280 is passed through a lead suture hole 680 at a first end portion 605 of the member 600, and a trailing suture 282 at a second end portion 620 is passed through a trailing suture hole 681. The intermediate portion 610 includes a prominence 630 on a surface 640 of the intermediate portion 610. The prominence 630 is in the form of a pair of transversely extending tabs 615, 616. The tabs 615, 616 facilitate alignment of the graft 290 with the fixation member 600 thus limiting any tendency of the fixation member 600 to rotate off-axis as it is being drawn through the bone tunnel. In addition, tabs 615, 616 extend into the femoral tunnel when the fixation member 600 is positioned against the cortex at the opening to the tunnel, thereby centering the member 600 on the bone. The material 281 may include suture material.

Figure 6A:
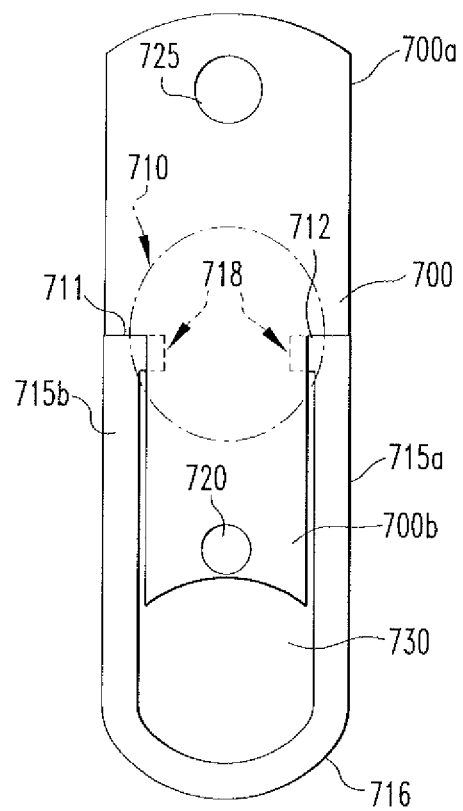
FIG. 6A is a plan view of an alternative embodiment of a fixation member.
Figure 6B:
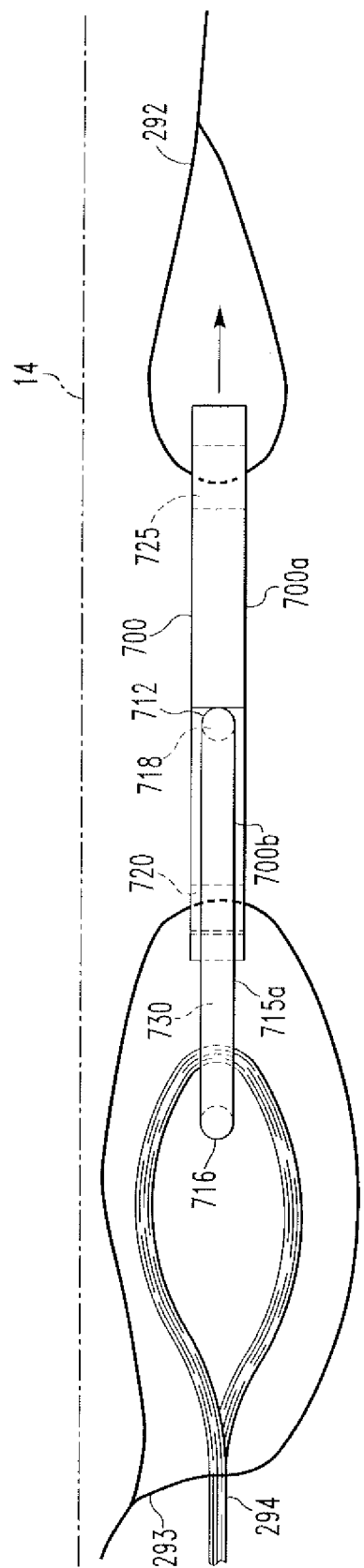
FIG. 6B is a side view of an alternative embodiment of a fixation member shown drawing the fixation graft through the femoral tunnel.

Referring to FIGS. 6A and 6B, an alternative fixation member 700 includes a U-shaped, rotatable hinge 716 coupled to and extending from an intermediate portion 710 of the fixation member 700. The U-shaped hinge 716 is a rigid, e.g., such as metallic, member which provides a movable mounting surface for directly connecting a tissue graft 294 thereto. The intermediate portion 710 and hinge 716 define a channel 730 therebetween through which the tissue graft is looped. A lead suture 292 is passed through a lead suture hole 725 at a leading, or first end 700a of the fixation member 700, and another suture 293 is passed through a trailing suture hole 720 at a trailing, or second end 700b, for flipping the fixation member 700 to position the fixation member 700 transversely to the bone channel opening. The U-shaped hinge 716 includes a pair of arms 715a, 715b and transversely extending hinge pins 711, 712 can be, for example, press-fit within the recesses 718 and/or pivotable about a common pin. When passed through a bone tunnel 14, the tissue graft 294 is evenly distributed on either side of the fixation member 700 to limit any tendency of the fixation member to pivot off-axis. When the fixation member 700 is flipped after passage through the bone tunnel 14, the U-shaped hinge 716 rotates relative to the remainder of the fixation member 700 such that the hinge 716 extends into the bone tunnel 14 while the remainder of the fixation member 700 lies against the bone surface, helping to center the fixation member 700 about the bone tunnel opening and center the tissue graft 294 within the bone tunnel 14.

Rather than coupling the tissue graft directly to the fixation member, suture attached to the tissue graft can be coupled to the fixation member. The suture can be coupled to the fixation member in the same manner as the coupling of the tissue graft directly to the fixation member, as described above.

The channels can be a variety of shapes, including circular, oval, elliptical and/or rectangular. The arms can also have a variety of shapes.

The leading and/or trailing ends can each be provided with one or more suture holes to facilitate positioning of the fixation member within the bone tunnel, and drawing the fixation member through the bone tunnel, and flipping the fixation member. A strand of suture can be extended between the opposing holes (FIG. 2b, 321a, 321b) to serve as a stop to enclose the otherwise open end of the channel 355 to secure the trailing end of the tissue graft bundle to the trailing end of the fixation member. The graft fixation member is formed from a biocompatible material such as titanium or PEEK, or a bioabsorbable material. The tissue graft may include autograft tissue, allograft tissue, or synthetic tissue. Additionally, instead of being positioned against the outer surface of the cortex at the opening to the femoral tunnel, the fixation member may be positioned inside the bone, thereby lying against the endosteal surface of the near cortex. As described above, suture material is used. However, other material known to one of ordinary skill in the art that is strong enough to withstand pulling the fixation member/tissue graft combination through the bone tunnel could be used.

Although the present disclosure relates to graft fixation members and methods of use in a multiple-bundle technique, the graft fixation members and methods can be used in a single bone tunnel technique, advantageously with the bone tunnel positioned as tunnel 200b as shown in FIG. 1.

The aforementioned tissue graft fixation procedure may be applicable to other parts of the knee or other parts of the human body requiring tissue reconstruction. Accordingly, other embodiments are within the scope of the following claims.

What is claimed is:

1. A graft fixation device, comprising:
a one-piece body configured and arranged for passage through a bone tunnel when oriented generally longitudinally with respect to the hone tunnel, and for residing against bone defining an opening to the bone tunnel when oriented generally transversely with respect to the bone tunnel,
the body consisting of a leading end portion consisting of a pair of rectangular arms with chamfered edges joined by a curved portion which collectively define a singular oval-shaped, closed-end, tissue graft opening, the curved portion defining a single suture hole, the tissue graft opening configured for housing a portion of a tissue graft such that the tissue graft is substantially evenly distributed about a longitudinal extent of the body so that the body maintains a generally longitudinal orientation during passage through the tunnel,
a trailing end portion of said body having a singular cross bar creating said singular oval shaped closed end tissue graft opening the pair of rectangular arms extending from the singular cross bar and defining an open-ended, tissue graft channel therebetween, the arms each defining one of opposing holes for receiving one or more strands of suture that are used to flip the graft fixation device after passage through a femoral tunnel such that the fixation member is positioned against a femur and centered about a femoral opening, and
the singular cross bar having rounded smooth edges tapered to a reduced thickness relative to the body providing a smooth surface for engagement, said singular cross bar comprising a maximum height that is less than a height of the body, wherein the height of the body has a dimension that is less than the width and length of the body.

2. The graft fixation device of claim 1 wherein the trailing end portion defines a hole.

3. The graft fixation device of claim 1, wherein the first closed-end, tissue graft opening comprises one of an oval, elliptical, or rectangular shape.

* * * * *